US012383641B2

(12) United States Patent
Truica-Marasescu

(10) Patent No.: US 12,383,641 B2
(45) Date of Patent: Aug. 12, 2025

(54) STERILIZATION OF PLANT MATERIAL

(71) Applicant: Cold Plasma Group Inc., Kingston (CA)

(72) Inventor: Florina Truica-Marasescu, Odessa (CA)

(73) Assignee: Cold Plasma Group Inc., Kingston (CA)

( * ) Notice: Subject to any disclaimer, the term of this patent is extended or adjusted under 35 U.S.C. 154(b) by 995 days.

(21) Appl. No.: 17/291,913

(22) PCT Filed: Nov. 8, 2019

(86) PCT No.: PCT/CA2019/051594
§ 371 (c)(1),
(2) Date: May 6, 2021

(87) PCT Pub. No.: WO2020/093168
PCT Pub. Date: May 14, 2020

(65) Prior Publication Data
US 2022/0001056 A1    Jan. 6, 2022

Related U.S. Application Data

(60) Provisional application No. 62/757,873, filed on Nov. 9, 2018.

(51) Int. Cl.
*A61L 2/14*    (2006.01)
*A01N 3/00*    (2006.01)
(Continued)

(52) U.S. Cl.
CPC .................. *A61L 2/14* (2013.01); *A01N 3/00* (2013.01); *A01N 25/00* (2013.01); *A01N 59/00* (2013.01);
(Continued)

(58) Field of Classification Search
CPC ............ A61L 2/14; A61L 2/007; A23B 2/103
See application file for complete search history.

(56) References Cited

U.S. PATENT DOCUMENTS 6,096,564 A  *  8/2000  Denes ....................... A61L 2/14
                                                    438/1
8,372,491 B2    2/2013  Rostaing
(Continued)

FOREIGN PATENT DOCUMENTS

CA       3064831 A1    12/2018
CA       3099845 A1    11/2019
(Continued)

OTHER PUBLICATIONS

English translation of CN-201105022-Y (Year: 2008).*
(Continued)

*Primary Examiner* — Sean E Conley
(74) *Attorney, Agent, or Firm* — Angela Lyon; Stephen J. Scribner

(57) ABSTRACT

Methods and apparatus for sterilizing plant material include disposing plant material in a sub-atmospheric pressure environment, dispersing a non-toxic, non-polymerizable gas into the sub-atmospheric pressure environment, applying an electric field to change the gas into cold plasma, and maintaining exposure of the plant material to the cold plasma until substantially sterilized plant material is obtained, wherein an amount of at least one active constituent in the plant material is substantially unchanged by the sterilizing. The plant material may be *Cannabis*.

35 Claims, 12 Drawing Sheets

(51) Int. Cl.
    *A01N 25/00*     (2006.01)
    *A01N 59/00*     (2006.01)
    *A23B 2/10*     (2025.01)
    *A23B 9/06*     (2006.01)
    *A23B 9/22*     (2006.01)
    *A61L 2/00*     (2006.01)

(52) U.S. Cl.
    CPC .............. *A23B 2/103* (2025.01); *A23B 9/06* (2013.01); *A23B 9/22* (2013.01); *A61L 2/007* (2013.01); *A61L 2202/11* (2013.01); *A61L 2202/122* (2013.01); *A61L 2202/14* (2013.01)

(56) References Cited

U.S. PATENT DOCUMENTS

| | | | |
|---|---|---|---|
| 9,308,285 | B2 | 4/2016 | Hancock et al. |
| 10,420,199 | B2 | 9/2019 | Wolfe et al. |
| 11,168,007 | B2 | 11/2021 | Lewis, III |
| 11,264,211 | B2 | 3/2022 | Lee et al. |
| 11,793,103 | B2 | 10/2023 | Wolfe et al. |
| 12,083,237 | B2 | 9/2024 | Lam et al. |
| 2009/0304950 | A1* | 12/2009 | Rostaing ............... A61L 2/14 427/575 |
| 2016/0262410 | A1* | 9/2016 | Hoefnagels ............ A23B 7/015 |
| 2017/0000167 | A1 | 1/2017 | Corrigan |

FOREIGN PATENT DOCUMENTS

| | | | |
|---|---|---|---|
| CN | 201105022 Y | * | 8/2008 |
| EP | 2840882 B1 | | 3/2018 |
| EP | 4108325 A1 | | 12/2022 |
| EP | 3332620 B1 | | 1/2023 |
| IL | 259283 A | | 6/2018 |
| WO | WO-8102809 A1 | * | 10/1981 |
| WO | 2013168038 A1 | | 11/2013 |
| WO | WO-2017218832 A1 | * | 12/2017 ............. A61L 2/007 |
| WO | 2019186568 A1 | | 10/2019 |
| WO | WO2019/216741 A1 | | 11/2019 |

OTHER PUBLICATIONS

Extended European Search Report for corresponding European Patent Application No. EP19882006.0 filed on Nov. 8, 2019.

Hertwig, C., et al., "Cold atmospheric pressure plasma and low energy electron beam as alternative nonthermal decontamination technologies for dry food surfacec: A review", Trends in Food Science & Technology 77, pp. 131-142, (2018).

International Search Report and Written Opinion for corresponding International Application No. PCT/CA2019/051594 filed on Nov. 8, 2019.

Australian Examination Report dated Nov. 13, 2024 for corresponding Australian Patent Application No. 2019375497.

* cited by examiner

STERILIZATION OF PLANT MATERIAL

RELATED APPLICATION

This application claims the benefit of the filing date of Application No. 62/757,873, filed on Nov. 9, 2018, the contents of which are incorporated herein by reference in their entirety.

FIELD

The invention relates to sterilization of plant material such that microorganisms can be reduced or eliminated from the plant material without significantly reducing active constituents.

BACKGROUND

Many species of plants are used for human or animal consumption as food, in beverages, as recreational mood-modifiers, and/or as medicines. Methods are known for cleaning and/or sterilizing plant materials so that they are safe for consumption, particularly human consumption. However, such methods may degrade flavor, nutrient value, and/or effectiveness of active (e.g., therapeutic) constituents in the plant material.

Use of recreational and medicinal *Cannabis* (*Cannabis sativa*, marijuana) is currently accepted in many countries. Medicinal *Cannabis* is used as a valid therapy for pain relief, nausea (e.g., chemotherapy-induced nausea), anorexia, anxiety, and as a mood modifier for subjects with cancer or human immunodeficiency virus (HIV). Recreational *Cannabis* is also used as a mood modifier. *Cannabis* is available in many different forms, such as in edibles (e.g., cookies, candies, chocolate), sublingual drops, a vaporized mist, or as a dry product for inhalation by smoking.

Various microorganisms can be carried on a plant's leaves and flowers. Exposure to certain microorganism through use/consumption of the plant may pose health problems. For example, microorganisms such as bacteria and/or mold(s) that are present on the surface of plant materials may lead to life-threatening pulmonary infections as a result of direct inhalation of smoke. This risk is especially serious for immunocompromised patients such as those with cancer or HIV.

Requirements of European and American pharmacopeias for herbal medicines are extremely stringent for microbial contamination of *Cannabis*. *Cannabis* producers are required to provide material that is nearly devoid of microbes. This stringent requirement is difficult to achieve under contemporary agricultural practices. Specific levels have been mandated, for example, for yeast, mold, gram negative bacteria, *Escherichia coli*, *Salmonella*, and others.

Accordingly, various sterilization methods have been tested for controlling microbial contamination of *Cannabis*. These methods include a combination of steam and heat treatment in autoclaves, such as a 50-min steam cycle and 30-min drying cycle at a temperature of 135° C. and a pressure of 316 kPa/3160 mbar (3.12 atm) (Ruchlemer R., et al., *Support Care Cancer* (2015) 23: 819-822); irradiation of dry *Cannabis* flowers using gamma radiation; exposure of *Cannabis* flowers to electron beams; and plasma treatments of hydrogen peroxide vapour at a relatively low temperature of 51° C. and a pressure of 30 Torr/40 mbar (0.04 atm) with electromagnetic excitation, performed in commercially available sterilizers (e.g., STERRAD 100NX, ASP, Johnson & Johnson, USA (Ruchlemer, R., et al., *Support Care Cancer* (2015) 23: 819-822)).

All of these methods have drawbacks which limit their usage. For example, sterilization by electron beam is cost-prohibitive. Sterilization using hydrogen peroxide vapour could lead to deposition of hydrogen peroxide on the sterilized *Cannabis*. Such residue could pose a health risk if ingested or the residual moisture may affect product quality. Exposure to harsh conditions of steam or gamma radiation results in heating of the *Cannabis* which, in turn, alters or destroys active constituents (e.g., cannabinoids, terpenes) and changes the smell, taste, and/or pharmaceutical properties of *Cannabis* sterilized in that manner.

SUMMARY

In one aspect, the invention provides a method for sterilizing plant material, comprising disposing plant material in a sub-atmospheric pressure environment that comprises at least one non-toxic, non-polymerizable gas, applying an electric field to the gas to create a cold plasma cloud, maintaining the plant material in the cold plasma cloud until substantially sterilized plant material is obtained, wherein an amount of at least one active constituent in the plant material is substantially unchanged by the sterilizing, and wherein sterilizing the plant material comprises killing microorganisms and/or rendering microorganisms inactive, without substantially etching the plant material.

In one embodiment, the sub atmospheric pressure is at least 0.01 torr. In one embodiment, the cold plasma does not deposit residue. In one embodiment, maintaining the plant material in the cold plasma cloud comprises exposure of the plant material on all sides to the cold plasma. In one embodiment, the plant material comprises leaves and/or flowers. In one embodiment, the plant material comprises seeds. In one embodiment, the applying an electric field comprises providing power to at least one of a pair of electrodes. In one embodiment, the electrodes are located inside the sub-atmospheric pressure environment. In one embodiment, one electrode is located inside the chamber and one is located outside the chamber. In one embodiment, the electrodes are located close to the sub-atmospheric pressure environment such that the electric field generated by the electrodes creates a cold plasma. In one embodiment, the electrodes are metal, current-carrying electrodes. In one embodiment, one electrode of the at least two electrodes is suited to allow gas and plasma to pass therethrough. In one embodiment, the plant material is substantially dry. In one embodiment, the plant material is disposed in the sub-atmospheric pressure environment in one or more single layer(s). In one embodiment, one or more single layer(s) of plant material are disposed on one or more metal, glass, or carbon-fibre shelves. In one embodiment, the one or more shelves are perforated or mesh. In one embodiment, each shelf of the one or more shelves has at least two electrodes in a spaced relationship. In one embodiment, the method further comprises exposing the substantially sterilized plant material to a sub-atmospheric pressure environment to evacuate plasma and plasma treatment byproducts. In one embodiment, the sub-atmospheric pressure is in a range of about 0.01 torr to about 10 torr. In one embodiment, the method further comprises controlling temperature of the sub-atmospheric pressure environment. In one embodiment, the gas is $H_2O$, air, dry air, $H_2$, $O_2$, $N_2$, Ar, He, Ne, Kr, Xe, or a combination thereof. In one embodiment, gas entering the sub-atmospheric pressure environment has a flow rate range of about 1 sccm to about 150 sccm. In one embodiment, a range of time of cold plasma treatment is from about 0.5 minutes to about 60 minutes. In one embodiment, the electric field is low frequency. In one embodiment, the electric field is in a range of about 20 kHz to about 60 kHz. In one embodiment, the electric field is in a range of about 40 kHz to about 50 kHz. In one embodiment, the electric field is high frequency. In one embodiment, the maintaining the plant material in the cold plasma cloud comprises maintaining a constant pressure of the gas. In one embodiment, the plant material comprises *Cannabis*. In one embodiment, the method further comprises tumbling, agitating and/or vibrating the plant material during the plasma treatment.

In one aspect, the invention provides an apparatus for sterilizing plant material, comprising a chamber having walls that define a cavity, the chamber having a gas inlet adapted to disperse at least one non-toxic, non-polymerizable gas into the chamber, and a gas outlet, at least two electrodes in a spaced relationship, the at least two electrodes adapted to be electrically connected to an AC power source and generate an AC electric field between them, at least one shelf disposed in the chamber between the at least two electrodes, the at least one shelf adapted to hold a single layer of plant material and to allow plasma to pass therethrough, a pump connected to the gas outlet, the pump adapted to establish a sub-atmospheric pressure of about 0.01 torr to about 10 torr in the presence of gas inflow in the chamber, wherein the at least two electrodes are adapted to generate a cold plasma cloud in the presence of the at least one non-toxic, non-polymerizable gas, the AC electric field, and the sub-atmospheric pressure, wherein the cold plasma cloud sterilizes the plant material by killing microorganisms and/or rendering microorganisms inactive, without substantially etching the plant material, and wherein an amount of at least one active constituent in the plant material is substantially unchanged by the sterilizing.

In one embodiment, the apparatus comprises at least two shelves and at least two pairs of electrodes, wherein each pair of electrodes comprises two electrodes adapted to be electrically connected to an AC power source and generate an AC electric field between them, and wherein each shelf of the at least two shelves is disposed between a respective pair of electrodes. In one embodiment, the shelves are suited to hold plant material in the cold plasma cloud such that the plant material is exposed to the cold plasma on all sides. In one embodiment, the gas is non-toxic, non-polymerizable, and when the gas is plasma, it leaves behind substantially no residue. In one embodiment, the gas is $H_2O$, air, dry air, $H_2$, $O_2$, $N_2$, Ar, He, Ne, Kr, Xe, or a combination thereof. In one embodiment, the gas inlet disperses the at least one gas into the chamber at a flow rate range of about 1 sccm to about 150 sccm. In one embodiment, the AC power source is low frequency. In one embodiment, the AC power source is in a range of about 20 kHz to about 60 kHz. In one embodiment, the AC power source is in a range of about 40 kHz to about 50 kHz. In one embodiment, the AC power supply is high-frequency. In one embodiment, the AC power supply is in a radio frequency (RF) of about 13.56 MHz. In one embodiment, the AC power supply is in a microwave frequency of about 2.45 GHz. In one embodiment, the plant material is *Cannabis*. In one embodiment, the plant material is hops. In one embodiment, the plant material comprises leaves and/or flowers. In one embodiment, the plant material comprises seeds. In one embodiment, the apparatus further comprises one or more metal, glass, or carbon-fibre shelves. In one embodiment, the one or more shelves are perforated or mesh. In one embodiment, one electrode of the at least two electrodes is suited to allow gas and plasma to pass therethrough. In one embodiment, the electrodes are located inside the chamber. In one embodiment, the electrodes are located close to the chamber such that the electric field generated by the electrodes converts the gas to a cold plasma. In one embodiment, the electrodes are metal, current-carrying electrodes. In one embodiment, the apparatus further comprises a temperature controller. In one embodiment, the apparatus further comprises a timer. In one embodiment, the apparatus further comprises an agitator that vibrates the shelves. In one embodiment, the apparatus further comprises a controller. In one embodiment, the controller controls one or more of gas flow rate, pressure, power, exposure time, and temperature. In one embodiment, the at least two electrodes comprise a plurality of electrodes and the at least one shelf comprises a plurality of shelves interspersed among the electrodes.

In one aspect, the invention provides a method for sterilizing plant material, comprising disposing plant material in a first reduced pressure environment, dispersing a gas into the first reduced pressure environment to raise the reduced pressure to a selected pressure, applying an electric field to change the gas into plasma, maintaining exposure of the plant material to the plasma until substantially sterilized plant material is obtained, wherein an amount of at least one active constituent in the plant material is substantially unchanged by the sterilizing.

In one embodiment of the above aspect, the plant material is substantially dry. In one embodiment, the plant material is disposed in one or more single layer(s). In one embodiment, the method further comprises exposing the substantially sterilized plant material to a second reduced pressure environment to evacuate plasma and plasma treatment byproducts. In one embodiment, the selected pressure is less than atmospheric pressure. In one embodiment, the selected pressure is in a range of about 0.01 torr to about 10 torr. In one embodiment, the method further comprises controlling temperature of the first reduced pressure environment. In one embodiment, the gas is non-toxic, non-polymerizable, and when the gas is plasma, it leaves behind substantially no residue. In one embodiment, the gas is $H_2O$, air, dry air, $H_2$, $O_2$, $N_2$, Ar, He, Ne, Kr, Xe, or a combination thereof. In one embodiment, gas entering the first reduced pressure environment has a flow rate range of about 1 sccm to about 150 sccm. In one embodiment, one or more single layer(s) of plant material are disposed on one or more metal, glass, or carbon-fibre shelves. In one embodiment, the one or more shelves are perforated or are mesh. In one embodiment, a range of time of plasma treatment is from about 0.5 minutes to about 60 minutes. In one embodiment, the electric field is low frequency. In one embodiment, the electric field is in a range of about 40 kHz to about 50 kHz. In one embodiment, the electric field is high frequency. In one embodiment, the maintaining exposure of the plant material to the plasma comprises maintaining a pressure of the gas constant. In one embodiment, the plant material is *Cannabis*.

In one aspect, the invention provides an apparatus for sterilizing plant material, comprising a chamber, a gas outlet including at least one pump that establishes a first reduced pressure in the chamber, a gas inlet that disperses at least one gas into the chamber to raise the reduced pressure to a selected pressure, at least two electrodes in a spaced relationship, at least one said electrode constructed to allow gas and plasma to pass therethrough, an AC power source electrically connected to the at least two electrodes, wherein a plasma field is generated between the electrodes in the presence of the at least one gas and an AC electric field between the electrodes, wherein the selected pressure is in a range of about 0.01 torr to about 10 torr.

In one embodiment of this aspect, the gas is non-toxic, non-polymerizable, and when the gas is plasma, it leaves behind substantially no residue. In one embodiment, the gas is $H_2O$, air, dry air, $H_2$, $O_2$, $N_2$, Ar, He, Ne, Kr, Xe, or a combination thereof. In one embodiment, the gas inlet disperses the at least one gas into the chamber at a flow rate range of about 1 sccm to about 150 sccm. In one embodiment, the AC power supply is low frequency. In one embodiment, the AC power supply is in a range of about 40 kHz to about 50 kHz. In one embodiment, the AC power supply is high-frequency. In one embodiment, the plant material is *Cannabis*.

BRIEF DESCRIPTION OF THE DRAWINGS

For a better understanding of the invention and to show more clearly how it may be carried into effect, reference will now be made, by way of example, to the accompanying drawings, wherein.

DETAILED DESCRIPTION OF EMBODIMENTS

Definitions

Figure 1A:
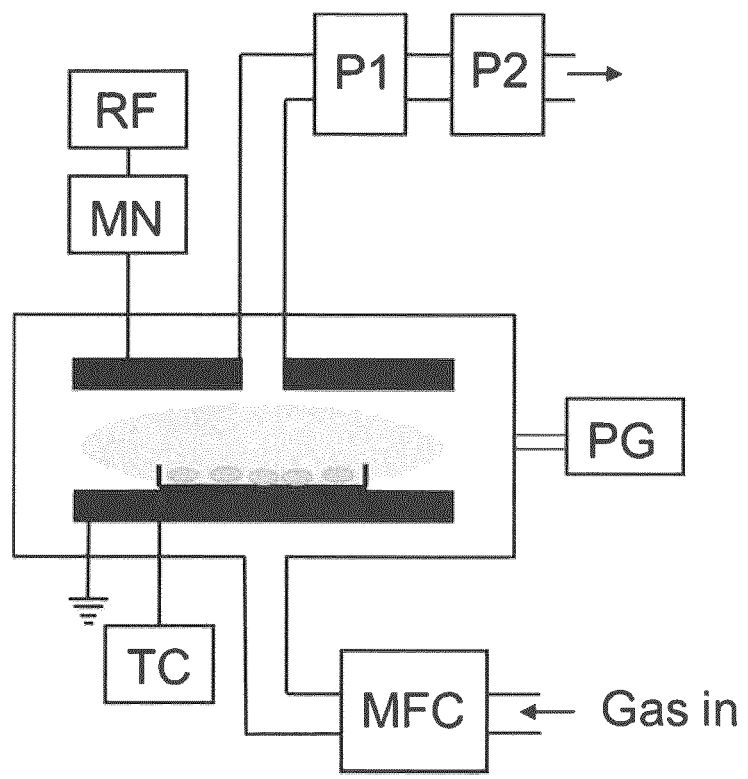
FIG. 1A shows a schematic diagram of a low-pressure plasma reactor used for the treatment of plant material, according to one embodiment.

As used herein, the term "ionized gas" refers to a gas that has been subjected to heat and/or an electric field such that some of its atoms have become ions. An ionized gas has a net overall charge.

As used herein, the term "plant material" refers to all parts of a plant including leaves, stems, flowers, seeds, roots, and fruit.

As used herein, the term "*Cannabis*" refers to any species of the genus *Cannabis*, including cultivars and hybrids thereof. Non-limiting, exemplary species are *Cannabis sativa* and *Cannabis indica*. Non-limiting, exemplary cultivars are CRM and TB-7. The term "*Cannabis*" also refers to plants commonly known as marijuana and hemp. The term "*Cannabis*" is intended to include the entire plant or any parts thereof, such as leaves, flowers, buds, seeds, etc.

As used herein, the term "active constituent" refers to a compound in plant material that has psychoactive and/or medicinal/pharmaceutical properties. Active constituents of *Cannabis* include, for example, cannabinoids such as, but not limited to, cannabidiol (CBD) and tetrahydrocannabinol (THC), terpenes, and flavonoids. The psychoactive and/or medicinal effect is obtained when *Cannabis* is consumed (e.g., inhaling smoke from burning the plant, ingesting the plant, or consuming products derived from or incorporating the plant). Such use, which may be recreational and/or pharmaceutical, may favour certain parts of the plant (e.g., flowers, leaves, buds). *Cannabis* strains have been bred to produce desired (e.g., minimal, maximal, etc.) levels of THC and/or other active constituents. Various products, including hashish and hash oil, can be made from the plant and contain one or more active constituents.

As used herein, the terms "sterilize", "sterilization", or "sterilizing" refer to eliminating or reducing numbers (i.e., populations) of microorganisms such as, e.g., yeasts, molds, and bacteria, also referred to herein as "microbes". Sterilization may include killing microorganisms or rendering them completely or substantially inactive, or completely or substantially harmless, i.e., unable to reproduce and/or ineffective at causing negative reactions when consumed.

As used herein, the term "plasma" refers to an ionized gas including approximately equal numbers of positively charged ions and negatively charged electrons, such that it is an electrically neutral medium of unbound positive and negative particles. Plasma may include ions, electrons, photons, radicals, and/or meta-stables. A plasma has a concentration of electrically charged particles (i.e., free electrons and positive ions) sufficient to affect the electrical properties and behavior of the ionized gas.

Plasma may exist under a wide range of conditions. For example, plasma may be produced by subjecting gas to an electric field, e.g., an electric field generated between electrodes. Specific properties of plasmas depend on parameters such electrical power, gas pressure, type of gas, electrode configuration, discharge configuration, etc.

Electrodes are placed to create a homogeneous (uniform) cold plasma cloud that is large enough to envelop the plant material from all sides. That is, the cloud should be large enough to contain the entire 3D dimension of the plant material to be treated.

Radio frequency (RF), microwave frequency, or low-frequency are examples of frequencies that can be used to generate cold plasmas under sub-atmospheric pressures. An example of a radio frequency range is 20 kHz to 300 GHz; a specific example is 13.56 MHz, which is the frequency at which an industrial RF band is centered. An example of a microwave frequency range is 2 to 60 GHz; a specific example is a microwave industrial band which is 2.45 GHz. An example of a low frequency range is 20 kHz to 60 kHz. In one embodiment, the frequency of the electric field is in a range of about 40 kHz to about 50 kHz. In one embodiment, the electric field is high frequency.

RF discharges, for example, can operate with or without electrodes inside a plasma reactor (i.e., a chamber), and can exist in a strongly non-equilibrium (non-thermal) regime.

Microwave frequencies can also be used to generate plasmas with electrodes placed outside the chamber. A microwave induced plasma discharge may be sustained by a high frequency electromagnetic field. Cold plasma generated using microwave frequencies can be non-thermal when operating at low gas pressures.

Generally, plasma exists in two main temperature regimes, non-thermal and thermal, which are sometimes referred to as cold or hot plasmas, respectively. The kinetic energy, which refers to the sum of translational, rotational, vibrational, and electronic energy of a gas constituent defines the temperatures of a gas and/or its constituents. When the mean kinetic energy (i.e., temperature) of ions is equal to the mean kinetic energy (i.e., temperature) of electrons in a plasma, the plasma is said to be in thermal equilibrium ("hot plasma" or "thermal plasma"). When the mean kinetic energy of electrons is significantly higher than that of ions, the plasma is said to be a non-equilibrium plasma ("cold plasma"). In non-thermal plasmas, electron temperatures are highest (e.g., 1 electron-volt (eV) to several eV). However, rotational excitation temperature, ion temperature, heavy particle temperatures, and the bulk gas temperature are all low (e.g., room temperature). Under such conditions, high energy electrons lead to the formation of active species (e.g., free radicals) inside the plasma. Examples of active species include atomic oxygen and hydroxyl ions.

Types of non-thermal (cold) plasma discharges include, but are not limited to, glow discharges, corona discharges, dielectric barrier discharges, gliding arc discharges, plasma jets, microwave discharges, and radio-frequency discharges. Among these, there are two main categories: (i) those operating at or near atmospheric pressure, and (ii) those operating under vacuum (e.g., sub-atmospheric pressure, or significantly lower than atmospheric pressure). Embodiments described herein work at sub-atmospheric pressures, also referred to herein as reduced pressure.

Plant materials have porous surfaces and microbial contamination can reside inside the pores. In order to effectively neutralize microbiological contaminants, plasmas must be able to penetrate inside the surface pores.

In accordance with embodiments described herein, it has been found that cold plasmas used under sub-atmospheric or reduced pressure environments are able to penetrate surface pores and achieve sterilization of plant material. In general, embodiments employ a large-area glow discharge in a reduced pressure environment using a non-polymerizable gas. One or more variables such as power, type of gas, reduced pressure, and duration of exposure are selected so that the cold plasma provides a sufficient concentration of active species surrounding the plant material. That is, the active species of the cold plasma cloud are able to reach substantially all surfaces and pores of the plant material. Under these conditions, microbiological contamination is completely or substantially killed, or rendered completely or substantially inactive, or completely or substantially harmless, such that the plant material is sterilized without significant changes in the physical properties and/or the concentrations of active ingredients contained in the plant material.

When a cold plasma is in contact with plant material, one or more result may be produced: (i) treatment; (ii) etching; and/or (iii) deposition. In (i) treatment, the plasma conditions are such as to generate low-energy active species which are capable of chemically interacting with the first few monolayers (e.g., up to 10 nm) of the plant material surface. Such treatment achieves the desired sterilization of plant material in accordance with embodiments described herein. Further, treatment is achieved without significant etching or deposition. (ii) Etching refers to removal of a selected thickness of the material through, e.g., molecular fragmentation. (iii) Deposition refers to new material being added on the surface of the plant material, e.g., via polymerization of the gas source (i.e., a polymerizable gas).

The plasma processing conditions, such as power coupled to the plasma, reduced pressure, gas nature, and treatment time may be selected such as to produce one of the three results mentioned above (treatment, etching, and/or deposition) at the surface of the plant material. These plasma-material interactions are not similar and it will be appreciated that each result may be achieved by implementing a different set of conditions. Accordingly, embodiments described herein are operated according to selected conditions that achieve the desired treatment (i.e., sterilization) of plant material without etching and deposition. Non-limiting examples of such selected conditions are provided in the Examples described below.

As described herein, cold plasma for sterilization of plant material provides a treatment environment that is capable of inactivating microbiological contaminants without substantially raising the temperature of the treated plant material. Because of the low-pressure and power conditions, the cold plasma cloud envelopes the plant material from all directions and provides free radicals and active species for inactivation reactions with microorganisms including mold, bacteria, and spores at the sites where they are present.

In regard to plasma discharges that occur at atmospheric pressure, there are several different kinds depending on reactor configurations and/or configurations of electrodes. Corona discharge, for example, is an atmospheric pressure, luminous plasma that has non-uniform discharges, which may appear near sharp points, edges, and along thin wires. If operated under appropriate conditions, this type of discharge can be used for the treatment of thermally sensitive materials. However, corona discharge non-homogeneity and the small size of the discharges make it poorly suited for treatment of large surfaces.

Dielectric Barrier Discharge (DBD) is similar to corona discharge in that it functions usually at or near atmospheric pressure without transitioning to an arc-type (hot) discharge. In the case of DBD, one or more dielectric layers are placed on top of the electrodes in the path of the electrical current. These layers prevent spark formation and prevent transition of DBD discharge into an arc-type (hot) plasma. Inter-electrode distance is typically low, in the range of 0.1 mm to a few centimeters. Some dielectric materials include glass, quartz, and ceramic. These types of discharges have been used to treat thermally sensitive materials; however, due to the very small inter-electrode distances, only flat and very thin materials that reside in the inter-electrode gap can be effectively treated. In addition, it is known that the presence of very small amounts of oxygen (e.g., a few ppm) in a discharge gas can make the discharge non-uniform and have a "streamer-like" character which leads to non-uniform treatment for large surfaces.

A gliding arc discharge plasma is another example of atmospheric pressure cold plasma that can be generated in multi-electrode reactors. Gliding arc reactors differ considerably from other non-thermal plasma sources. They are based on an auto-oscillating periodic phenomenon that develops between at least two diverging electrodes submerged in a laminar or turbulent gas flow. First, the discharge self-initiates at the upstream narrowest gap. Then, the discharge forms a plasma column connecting the electrodes of opposite polarity, which is dragged by the gas flow towards the diverging downstream section. The discharge eventually extinguishes and momentarily reignites itself at the minimum distance between the electrodes, starting a new cycle. These types of plasmas can also be used for the treatment of thermally sensitive materials; however, the reactors are usually small and compact, which complicates their usage for the treatment of large surfaces. In addition, the materials to be treated are not in contact with a plasma, as they are placed downstream from the reactor and in contact with what is called a "remote plasma". Remote plasmas differ from traditional plasmas, as they contain only reactive species and photons, without electrons or ions being present.

The same applies for plasma jets, also called sometimes plasma pens, or plasma needles. These discharges are special configurations of previously described discharges. The active regions of the discharges are blown out by flowing auxiliary gases which pull the particles outside of the electrode areas forming streams of active particles burning as small jets. Because of their particular configurations, plasma jets, needles, pens and gliding arcs are small in size, and very directional and therefore not suited for the treatment of three dimensional objects, such as plant material.

One factor to consider when choosing a suitable plasma for a specific treatment is mean free path, and its relationship with pressure of the gas. Mean free path is the average distance travelled by a moving particle (such as an atom, a molecule, a radical or photon) between successive impacts (collisions), which modify its direction or energy or other particle properties. For radicals, a collision often leads to its neutralization through recombination reactions. For plasmas operating at or near atmospheric pressure, mean free path at room temperature is around 60 nm. This means that a radical will be able to travel in average only 60 nm from its point of origin before being neutralized. Plasma treatment relies on the interaction between the particles generated within the plasma bulk and the surface; therefore, the free mean path and its relationship with the roughness of the surface becomes important. Materials with smooth surfaces will be effectively treated using atmospheric pressure plasmas; however, for the treatment of materials containing porous structures, such as plant material, a plasma operating at much lower gas pressures becomes more suitable. For example, plasmas operating under low vacuum (low pressures, sub-atmospheric pressures) of 0.8 mtorr to 10 torr can have free mean paths of 0.4 micrometers ranging up to 5 mm.

Embodiments

As described herein, a sterilization apparatus and method has been developed that uses a non-thermal (cold) plasma. The cold plasma sterilizes plant material surfaces without changing the physical and chemical properties of the plant material. Treatment with cold plasma as described herein does not change the visual appearance and smell of the plant material. Since certain plant material, such as flowers and leaves, is thermally sensitive, exposure to hot plasma would negatively impact its visual appearance and smell.

Embodiments are described herein primarily with respect to *Cannabis* and hops. However, it is expected that the methods and techniques described are broadly applicable to a wide range of plant species used for human and animal consumption, as foods, medicines, and/or mood-altering products. Accordingly, the invention is applicable to plant material other than *Cannabis* or hops.

Terpene profiles of hops and *Cannabis* share some major components as shown in Table 1. Primarily myrcene makes up to 52% of the composition in hops and 58% of the composition in *Cannabis*. Other shared components include linalool, α-pinene, β-pinene, α-humulene (a major component in hops), β-caryophyllene, and limonene. Due to the shared terpene components, hop flower samples have been used to study effects of plasma sterilization treatment on terpenes. Example 3 describes such a study and results are shown in FIGS. 4A-4H and 5A-5H. The results depicted in FIGS. 4A-4H and 5A-5H indicate that plasma sterilization as described herein had substantially no effect on the concentration of all tested terpenes.

A challenge of plasma treatment for sterilization of plant material is avoiding damage to physical-chemical properties of the material to be treated. Embodiments described herein provide methods for sterilizing plant material, such as *Cannabis*, to reduce the level of or eliminate active microorganisms (such as, e.g., yeasts, molds, and bacteria (e.g., anaerobic bacteria species, and bile-tolerant gram negative bacteria)) present, without significant damage to the physical-chemical properties of the material. In the case of *Cannabis*, the embodiments provide a plasma environment that is optimized (e.g., contains appropriate plasma components such as ions, electrons, radicals, photons) for such sterilization. Accordingly, populations of microorganisms are reduced to required safety levels without significantly altering the quantities (e.g., concentrations) of active constituents, and accordingly, without significantly degrading the desired properties (i.e., psychological and/or pharmaceutical activity when consumed) of *Cannabis*. That is, whereas some active constituents may be degraded and rendered inactive, the embodiments ensure that any degradation is minimized such that the overall psychological and/or pharmaceutical activity of the *Cannabis* is substantially maintained. The substantial volume of flowers represents a significant challenge that is met by the embodiments described herein. Flower surfaces have convoluted 3D structures that include large peaks and valleys. Microbes are present on the surfaces of flowers, which includes residing in pores. Sterilization by cold plasma includes penetration inside these pores.

Embodiments generally include disposing *Cannabis* in a vacuum chamber, dispersing a non-toxic, non-polymerizable gas into a reduced pressure environment in the chamber, applying an electric field that changes the gas into a cold plasma, maintaining exposure of the *Cannabis* to the cold plasma until substantially sterilized *Cannabis* is obtained. Embodiments substantially preserve active constituents in *Cannabis*. That is, the amount or properties of at least one active constituent in *Cannabis* is substantially unchanged by the sterilizing.

In one embodiment, plant material (e.g., *Cannabis*, hops) is substantially dry prior to plasma treatment. In one embodiment, the plant material is disposed in the chamber in a single layer or with minimal overlap so that the plasma can effectively reach all the material, to ensure proper sterilization. In one embodiment, one or more single layer(s) of plant material are disposed on one or more shelves within the chamber. Shelves should not impede the exposure of the plant material to the plasma, and may be made of mesh or otherwise constructed so as to substantially allow plasma to pass through. In one embodiment, the plant material is tumbled and/or vibrated during the plasma treatment to assist with exposure of all surfaces to the plasma. In one embodiment, the plant material is centrally located in the cold plasma cloud.

In one embodiment, after disposing the plant material in the chamber and prior to introducing a gas, the chamber is placed under reduced pressure. Evacuation of air from the chamber assists with providing a consistent atmosphere once the gas is introduced. In one embodiment, the chamber is evacuated again after the plasma treatment, to remove plasma and plasma treatment byproducts.

Embodiments may use a gas that is non-toxic and non-polymerizable. Also, the gas may be chosen so that little or no residue is left behind after plasma treatment. Examples of suitable gases include, but are not limited to: water, air, dry air, $H_2$, $O_2$, $N_2$, Ar, He, Ne, Kr, Xe, or a combination of two or more thereof.

The amount of time that plant material is exposed to plasma to achieve sterilization is dependent on the quantity and type of plant material being sterilized. For example, *Cannabis* flowers or buds may require more time to expose all surfaces sufficiently, when compared to leaves. If the plasma treatment lasts for a long time, the sterilized plant material may appear visually different from the unsterilized plant material. A suitable time period is one that allows for substantial sterilization but does not change the visual appearance and/or smell of the plant material, and preserves and maintains the psychoactive and/or pharmaceutical properties active constituent(s). An example of a time range for plasma treatment is from about 0.5 minutes to about 60 minutes. In particular, it is noted that a change in the colour and/or smell of *Cannabis* after sterilization may provide an indication of a change in amount of active constituent, and thus a change (reduction) in psychological and/or pharmaceutical activity of the *Cannabis*. Thus, a feature of the embodiments is that the colour and smell of *Cannabis* are not substantially changed through plasma sterilization.

Embodiments are generally carried out in a sealed compartment (i.e., a "chamber") in which a reduced pressure can be established, and which contains the gas(es) and plasma. In one embodiment, the selected pressure for plasma treatment is less than atmospheric pressure. In one embodiment, the selected pressure is in a range of about 0.02 torr to about 10 torr (10 torr is equivalent to 13.3 mbarr or 0.01 atm). In one embodiment, once the plant material is placed under reduced pressure, the gas is introduced at a selected flow rate. In one embodiment, the selected flow rate is in the range of about 1 sccm to about 150 sccm (standard cubic centimeters per minute). The flows of gas entering and exiting the chamber may be selected to set the chamber at a selected pressure level. In some embodiments, gases and by-products are continuously removed from the plasma chamber by the vacuum pumps, and a fresh supply of gas is flowed into the chamber while the selected pressure is maintained.

To form plasma, the gas (or gases) are excited into cold plasmas by exposure to an electric field (also referred to herein as an electromagnetic field). The electric field may be created between electrodes by applying power to the electrodes. In one embodiment, alternating current (AC) at low-frequency (e.g., 20 kHz-60 kHz) is used. In another embodiment, AC power at high frequency in the radio frequency (RF) range or microwave range is used. For example, frequencies of 13.56 MHz and 2.45 GHz, respectively, may conveniently be used. However, other RF and microwave frequencies may of course be used. One factor that may be considered is the distance between the electrodes in which the plasma is generated, wherein higher frequencies (shorter wavelengths) may be used at shorter distances. The electromagnetic field may be operated either in continuous or pulsed mode. Application of the electromagnetic field can be made with either capacitively-coupled electrodes or inductively-coupled electrodes. Exposure of plant material to reactive species generated within the plasma at low pressures for a set period of time effectively sterilizes the plant material. The electrodes may be metal, current-carrying electrodes. The electrodes may be located inside a chamber where a sub-atmospheric pressure environment is created and where the cold plasma cloud is generated. In one embodiment, the electrodes are located close to the sub-atmospheric pressure environment such that the electric field between the electrodes creates a cold plasma. In one embodiment, there is a barrier between the electrodes and the environment, wherein the electric field is able to penetrate the barrier. An example of such a barrier is glass.

Temperature may be controlled in the chamber to avoid high temperatures that could negatively affect one or more properties of the sterilized plant material. Temperature may be controlled by controlling one or more of pressure, power of the electromagnetic field, frequency of the electromagnetic field, and/or the duration of treatment. If a high temperature is reached during plasma treatment, the resulting sterilized *Cannabis* may appear or smell different from unsterilized *Cannabis*, or have reduced psychoactive and/or pharmaceutical properties.

In one embodiment, the apparatus and method of the invention include a controller, which controls one or more of gas flow rate, pressure, power, exposure time, and temperature.

FIG. 1A shows an embodiment wherein plant material is placed on the bottom electrode (e.g., ground), or on a support elevated above the bottom electrode. A reduced pressure environment may be induced. A cold plasma is generated between the top and bottom electrodes. A power supply provides power to the electrodes via a matching network. A pressure gauge may be used to monitor pressure in the chamber. A mass flow controller controls gas flow into the chamber and a thermocouple is used to monitor the temperature inside the chamber.

Figure 1B:
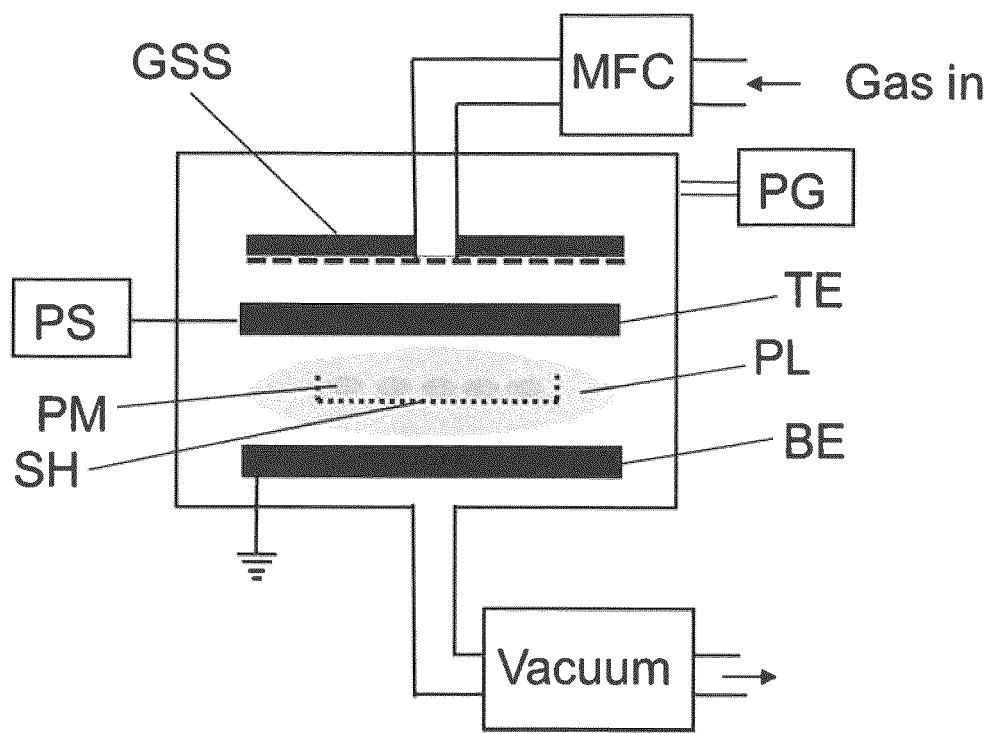
FIG. 1B shows a schematic diagram of a low-pressure plasma reactor used for the treatment of plant material, according to one embodiment.

FIG. 1B shows another embodiment of a sterilization apparatus. In contrast to the embodiment shown in FIG. 1A, in this embodiment plant material is placed onto a perforated holder (e.g., mesh shelf) made of a suitable non-ferrous material, such as glass, glass fiber, ceramic, carbon composite, etc. The sample holder is raised relative to the electrode and placed in the bulk region of the cold plasma cloud. In this position, the contribution of ions and electrons to the treatment is minimized, as there is no potential difference between the plasma region and the holder. Openings in the sample holder are sufficiently large to allow the active species and photons contained in the plasma to have access to all sides of plant parts to perform the sterilization. To further ease the access of those active species to the entire surfaces of the plant parts, the plant material can be agitated, tumbled, or vibrated. Similarly, the holder of the plant material can be vibrated and/or tilted around one or two axes, or any suitable motion.

Embodiments described herein are different from commercial sterilization processes used in the medical industry, such as STERRAD 100NX, ASP, Johnson & Johnson, USA (STERRAD® 100NX™ Sterilizer System "User's Guide" June 2007, p. 25, available at: https://www.udh.med.sa/advices/USER'S_GUIDE_STERRAD_100NX.PDF). The STERRAD system relies on the use of antiseptic and potentially toxic oxidizing compounds, such as hydrogen peroxide. In contrast, the embodiments use non-toxic plasma species (e.g., ions, metastables, radicals, photons) to initiate chemical and physical reactions that cause inactivation and/or destruction of microorganisms. Due to the use of non-toxic gases, the embodiments provide a method wherein no harmful residue is left on the sterilized *Cannabis* after the sterilization treatment.

Another way that the embodiments are different from the STERRAD system is that the gas pressures used in the embodiments are significantly lower than those used with the STERRAD 100NX system. For example, in some embodiments, the gas pressures are at least one order of magnitude lower. These lower pressures affect the energy profiles of the plasma species and their outcome (Conrads H., et al., *Plasma Sources Sci. Technol.* (2000) 9:441-454).

Plasma processes are considered cost-effective, environmentally-friendly and require a relatively low capital investment. A plasma system can be made compact and fully automated with a foot print which is scalable with the treatment speed requirements.

Plasma treatments have a very shallow penetration depth, typically only a few nm (approx. $10^{-9}$ m) in organic materials. Terpene molecules are distributed throughout the entire volume of the flowers, which have typical thicknesses in the order of 1 cm ($10^{-2}$ m) or more. Therefore, even if plasma exposure led to degradation, it would occur for only a $10^{-7}$ fraction of all terpene molecules present within the flower (assuming a relatively uniform distribution), which is negligible. In contrast, sterilization methods that rely on the action of heat, or that include absorption of a particular form of radiation (e.g., gamma rays, ultraviolet, or microwaves), affect a larger portion of the flowers or the entire volume of the flowers. This effect on a larger portion is why sterilization methods that rely on the action of heat are likely to induce a degradation of terpenes and cannabinoids during treatment.

The following working examples further illustrate the invention and are not intended to be limiting in any respect.

Example 1

Apparatus for Sterilizing Plant Material by Plasma Treatment

FIG. 1A shows a diagram of the apparatus used to conduct sterilization trials on two strains of *Cannabis* flowers (CRM and TB-7) using representative gases $N_2$, air, $O_2$, and a mixture of $O_2$ and $H_2$.

An air-tight cylindrical aluminium/steel vacuum chamber (VC) was fitted internally with two circular capacitively-coupled electrodes 22 cm in diameter, separated by 3.4 cm, referred to as the top electrode (TE) and the bottom electrode (BE). The top electrode allowed gas to pass through. The bottom electrode was grounded and was constructed to allow gas and plasma to pass through. Plant material (PM) was placed on the bottom electrode. The plasma generated between the top and bottom electrodes is shown as PL. A turbo-molecular pump P1 (Edwards, STP-iXA2206C), backed by a two-stage rotary vane pump P2 were used to create a sub-atmospheric pressure environment in the chamber. A 13.56 MHz power supply (RF) provided power to the electrodes via a matching network (MN). A pressure gauge (PG) was used to monitor pressure in the chamber. A mass flow controller (MFC) controlled gas flow into the chamber, a thermocouple (TC) was used to monitor the temperature inside the chamber.

A *Cannabis* sample (10 g) was placed on the bottom electrode, the chamber was closed and was placed under reduced pressure using P1 and P2. The chamber was evacuated to a base pressure of <$10^{-6}$ torr, as measured by the pressure gauge (PG). Pumping time was approximately 30 min.

A flow of a high-purity feed gas was introduced into the chamber using the flow controller MFC (Vacuum General Inc.). A selected operating pressure of 300 mtorr and gas flow rate of 10 sccm were attained and maintained during plasma treatment using a butterfly throttle valve (MKS Instruments 253A-2-50-2 Exhaust Throttle Valve/Control Valve), in combination with a pressure gauge (Baratron, MKS Instruments). The power applied to the electrodes varied between 10 and 100 W. Treatment durations were varied between 2 and 30 min. In trials with treatment durations of longer than 30 min, the *Cannabis* flower samples had visually apparent thermal damage.

Example 2

Analysis of Microbial Contaminants Remaining in Samples after Sterilization

Results showed that populations of all microbial species decreased relative to duration of plasma treatment for both *Cannabis* strains (CRM and TB-7) that were treated. Microbes displaying more resilience towards plasma treatment were yeast and molds. Microbes displaying less resilience towards plasma treatment were bile-tolerant gram negative bacteria. *Escherichia coli* and *Salmonella* were not present in the unsterilized *Cannabis* samples. Surviving populations of anaerobic bacteria and bile-tolerant gram negative bacteria decreased quickly with plasma treatment and reached levels that were below the threshold level (50,000 cfu/g) that is considered safe. Surviving populations of yeast and molds required longer treatment durations.

Figure 2:
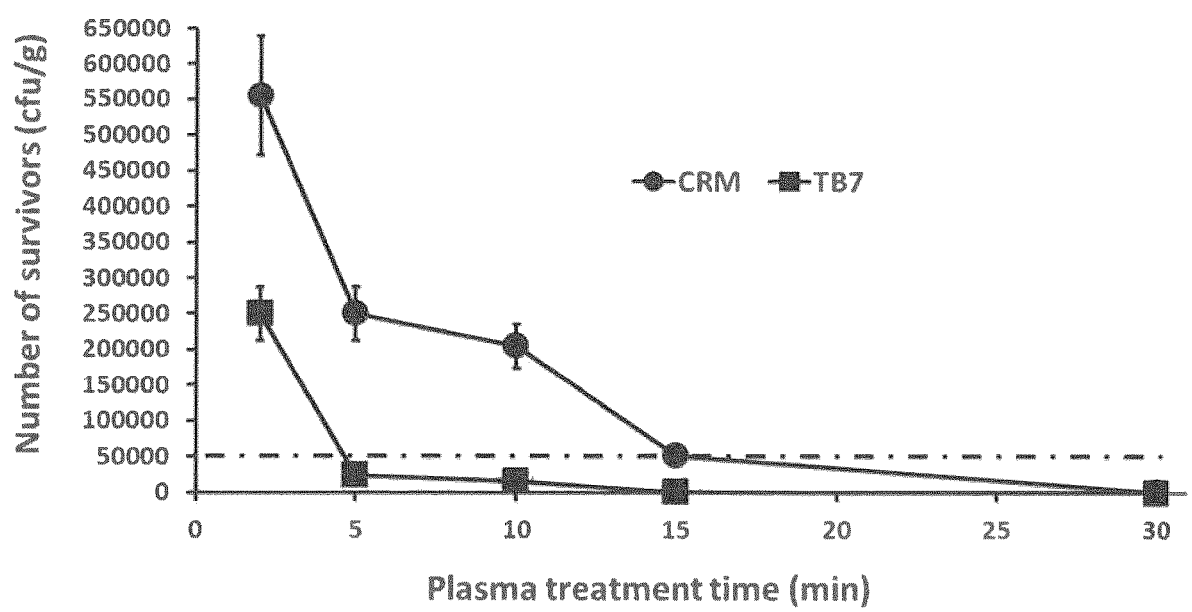
FIG. 2 shows survival curves of total yeast and mold species versus plasma treatment duration, for CRM and TB-7 *Cannabis* samples, using the apparatus of FIG. 1A, wherein circular symbols are the results for CRM flowers and square symbols are the results for TB-7 flowers.

A typical example of a survival curve for yeast and mold is presented in FIG. 2, for the case of an oxygen plasma treatment for up to 30 min, at 300 mtorr and nominal power of 100 W. As shown in FIG. 2, yeast and mold populations decreased steadily relative to treatment time although at different rates for the two *Cannabis* flower samples (CRM and TB-7) that were tested.

In the case of TB-7 flowers, plasma treatment for only 5 min decreased the surviving population of yeast and mold below the 50,000 cfu/g level that is considered to be safe. In the case of CRM flowers, plasma treatment for more than 15 min was required to decrease the surviving population of yeast and mold below the 50,000 cfu/g level. While different initial levels of contamination (250,000 cfu/g for TB-7 vs 550,000 cfu/g for CRM) might explain the observed difference, the different morphology of the flowers could also play a role. CRM flowers have pores with smaller inner diameters than the TB-7 flowers, which makes it more difficult for plasma to penetrate inside the flowers and inactivate the microorganisms that are present there.

Figure 3:
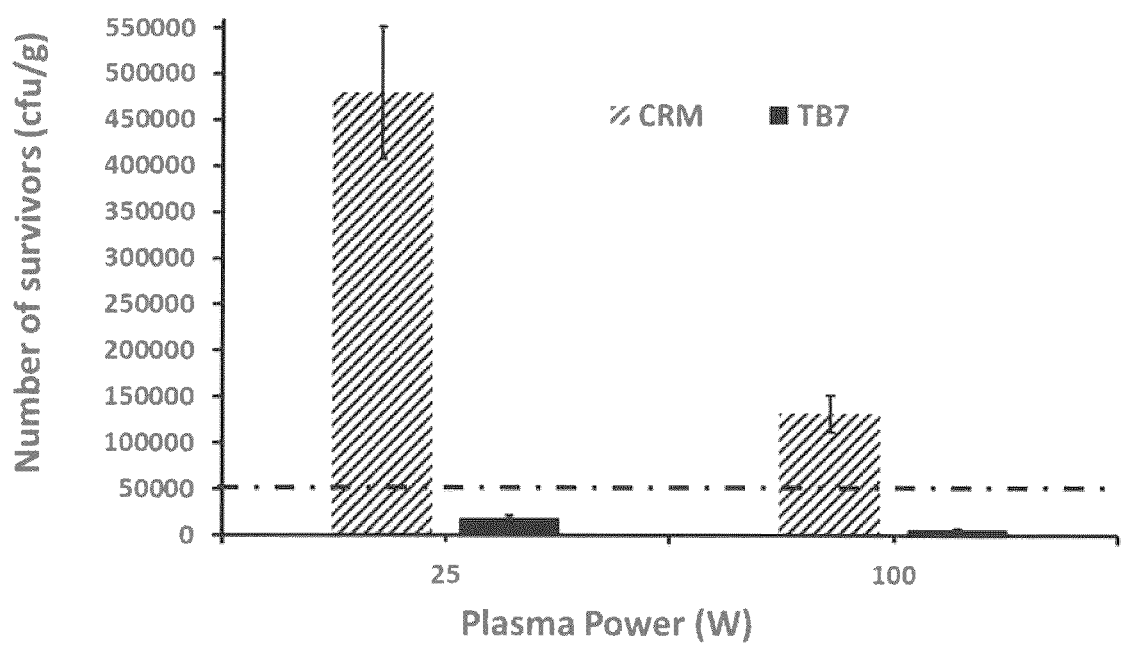
FIG. 3 shows a plot of total number of survivors of yeast and mold species versus plasma power, for CRM and TB-7 *Cannabis* strains that were exposed for 10 min to a plasma operated in oxygen gas at 300 mtorr and nominal powers of 25 W and 100 W.
Figure 4A:
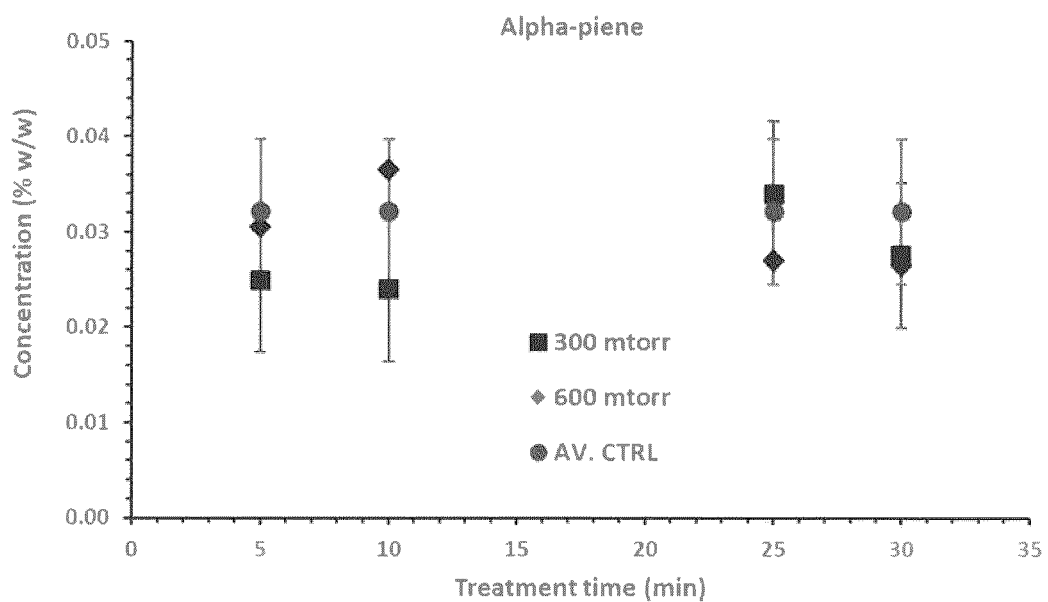
FIGS. 4A-4H show plots of average values for terpene concentrations as a function of plasma treatment time for A) α-pinene; B) β-myrcene; C) β-pinene; D) limonene; E) linalool; F) geraniol; G) β-caryophyllene; and H) humulene, expressed as weight percent; control (untreated) samples are identified by circles, while treated samples are identified by square symbols for $O_2$ gas pressure of 300 mtorr and plasma power of 100 W, and by diamond symbols for $O_2$ gas pressure of 600 mtorr and plasma power of 100 W.
Figure 4B:
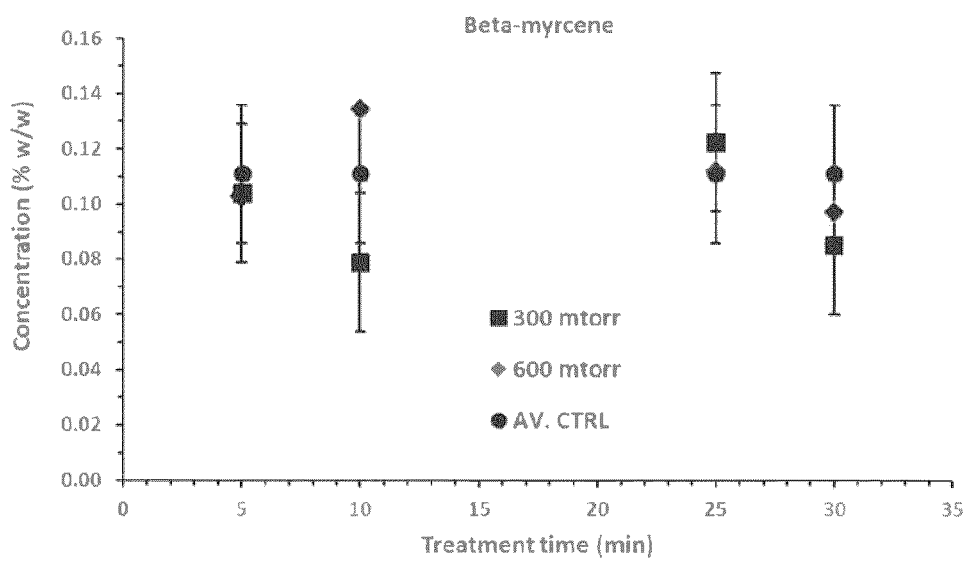
Figure 4C:
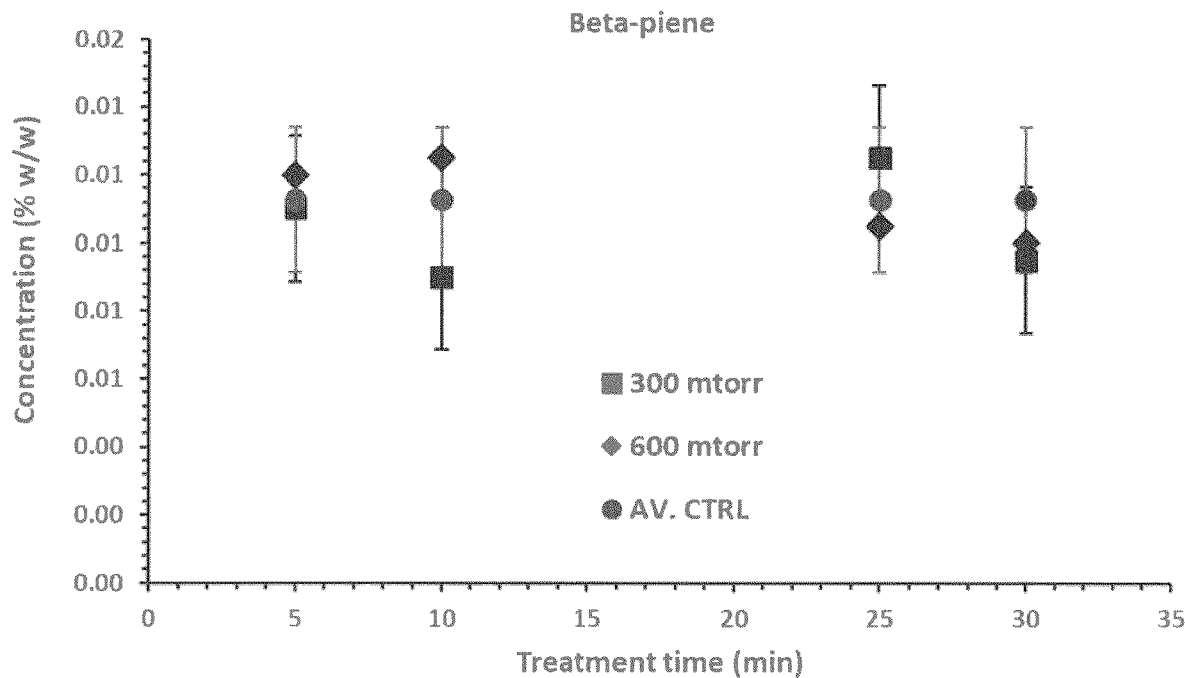
Figure 4D:
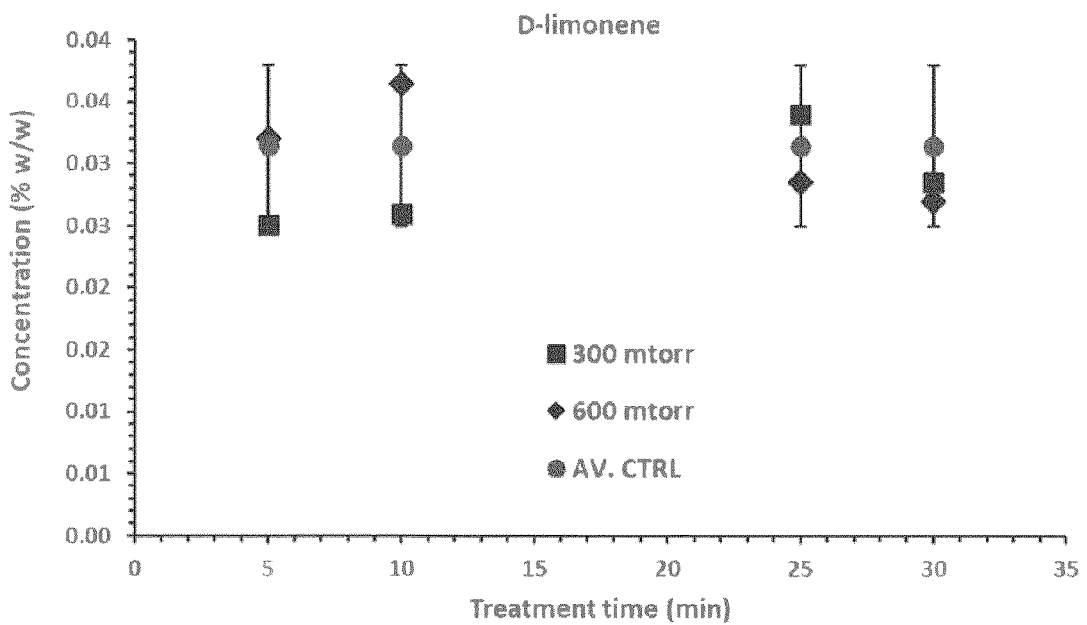
Figure 4E:
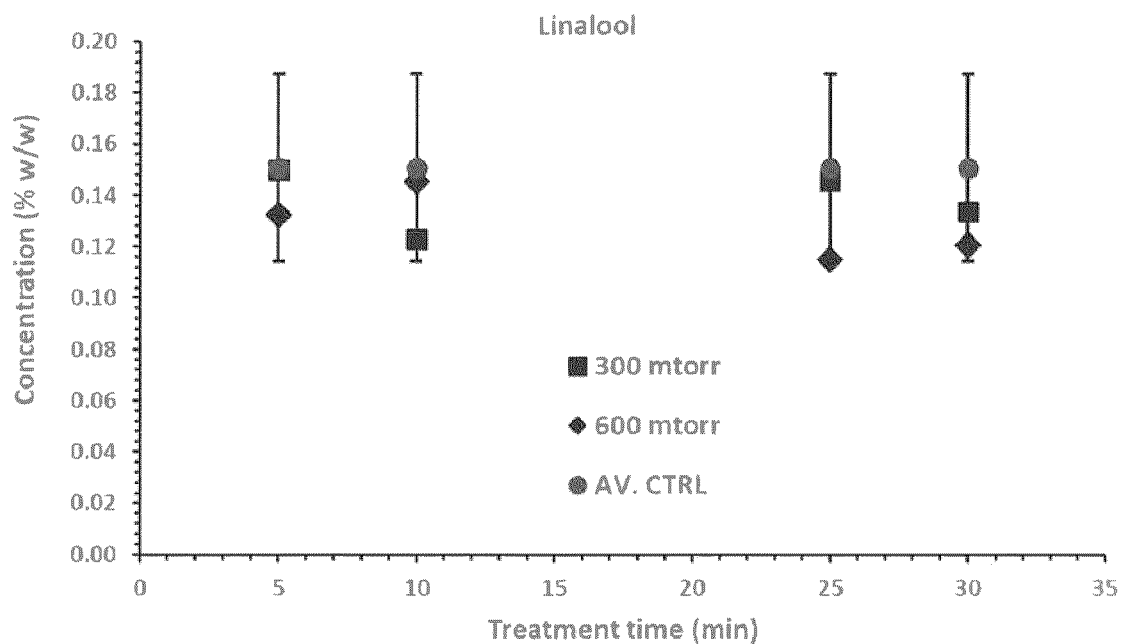
Figure 4F:
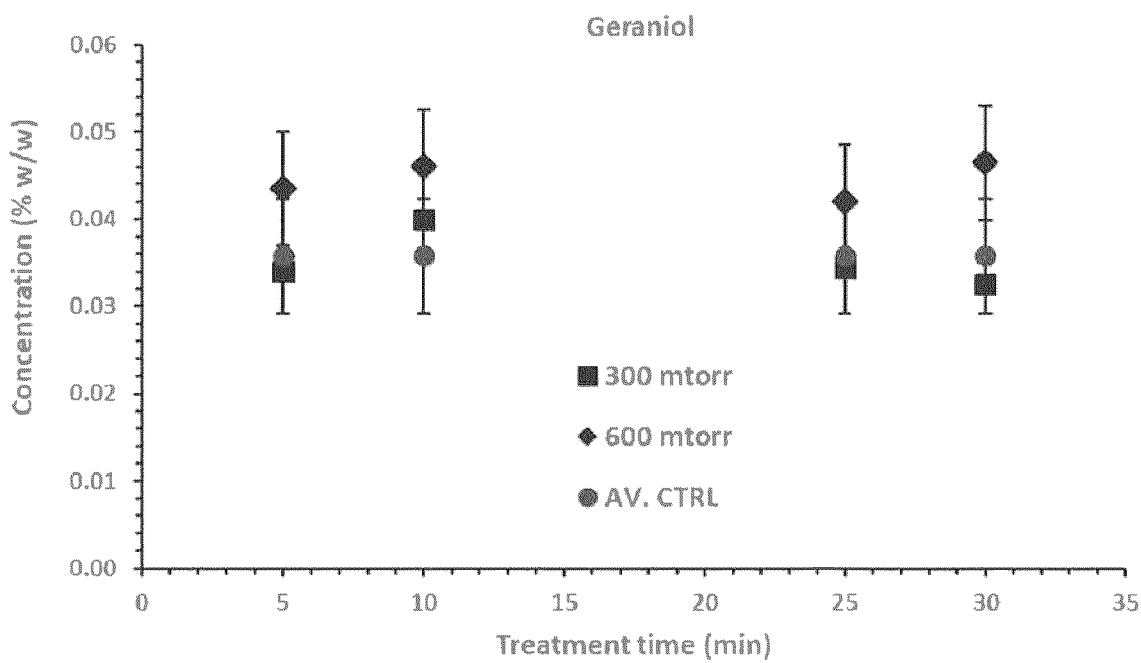
Figure 4G:
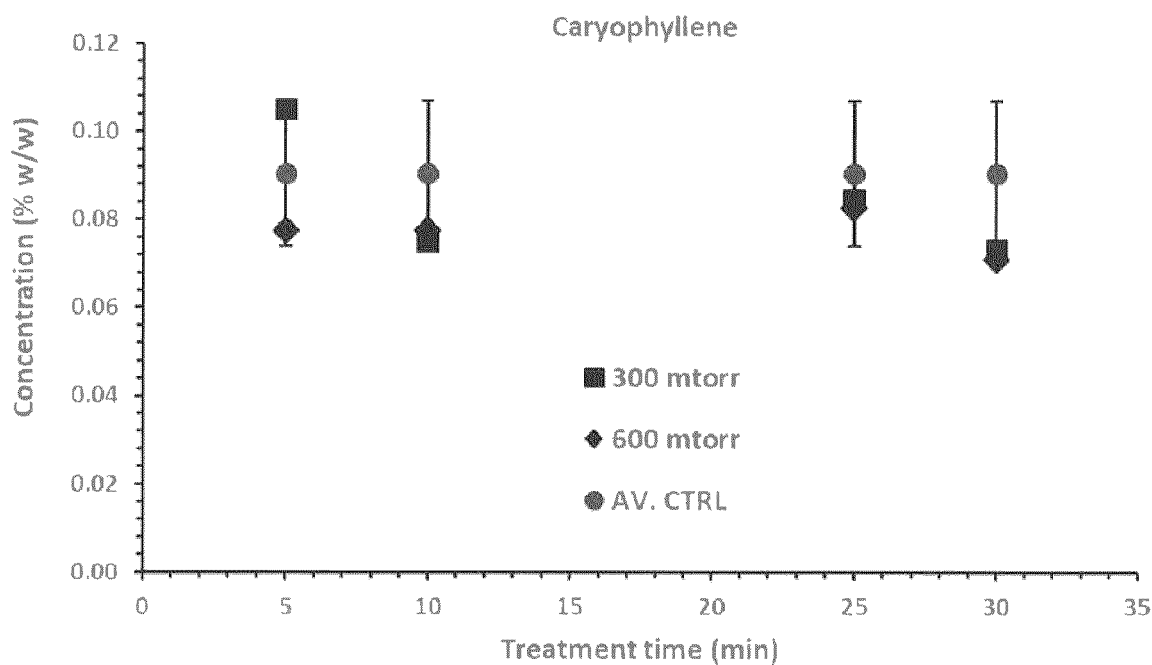
Figure 4H:
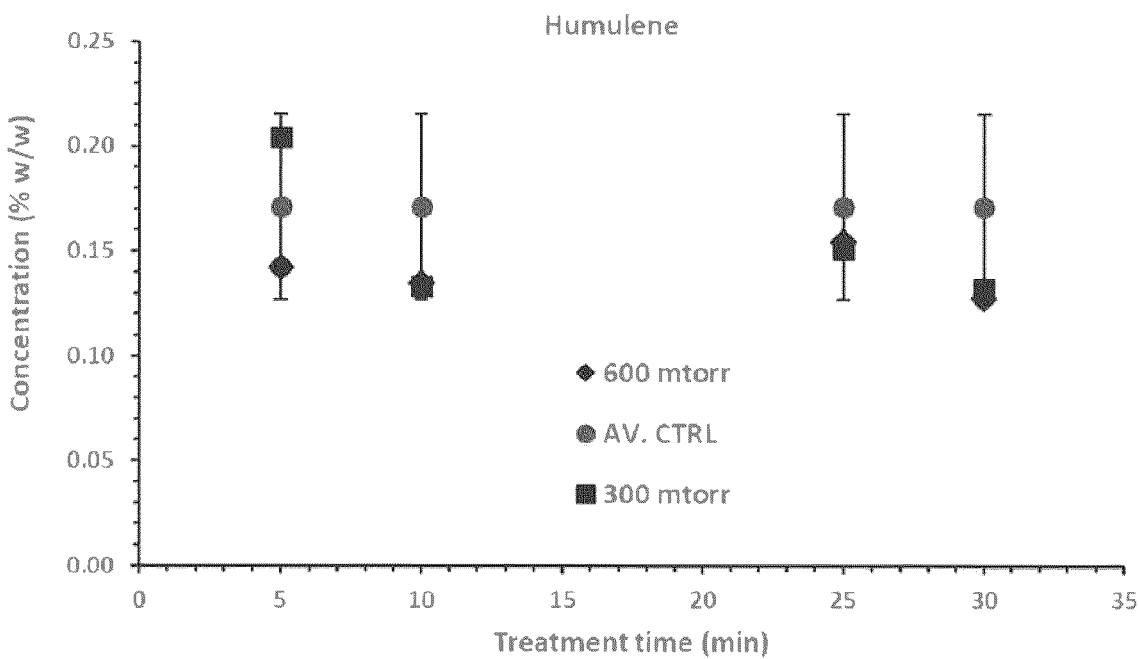
Figure 5A:
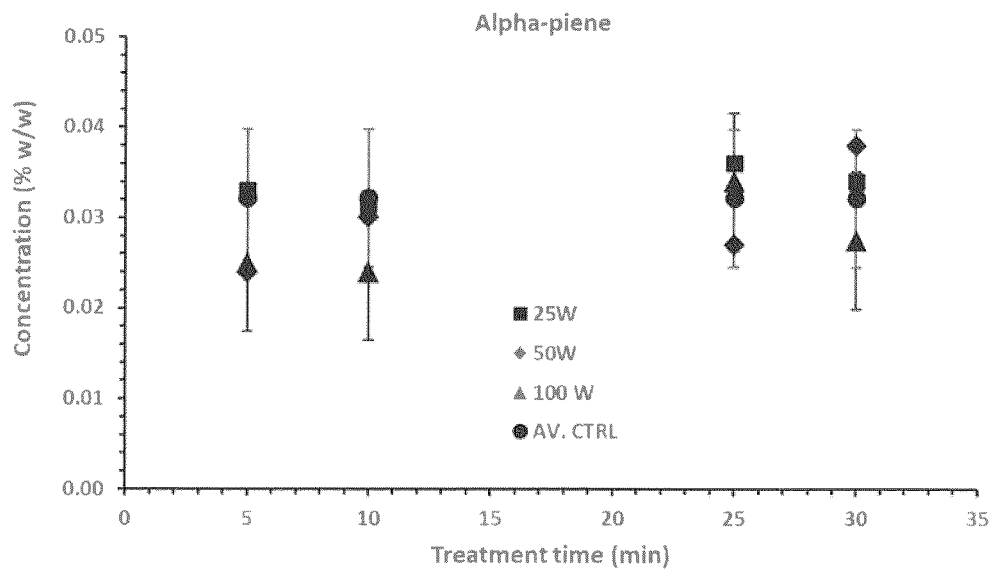
FIGS. 5A-5H show plots of average values for terpene concentrations as a function of the plasma treatment time for A) α-pinene; B) β-myrcene; C) β-pinene; D) limonene; E) linalool; F) geraniol; G) β-caryophyllene; and H) humulene, expressed as weight percentage; control (untreated) samples are shown as circles, treated samples are identified with square symbols for plasma power of 25 W, diamond symbols for plasma power of 50 W, and triangle symbols for plasma power of 100 W.
Figure 5B:
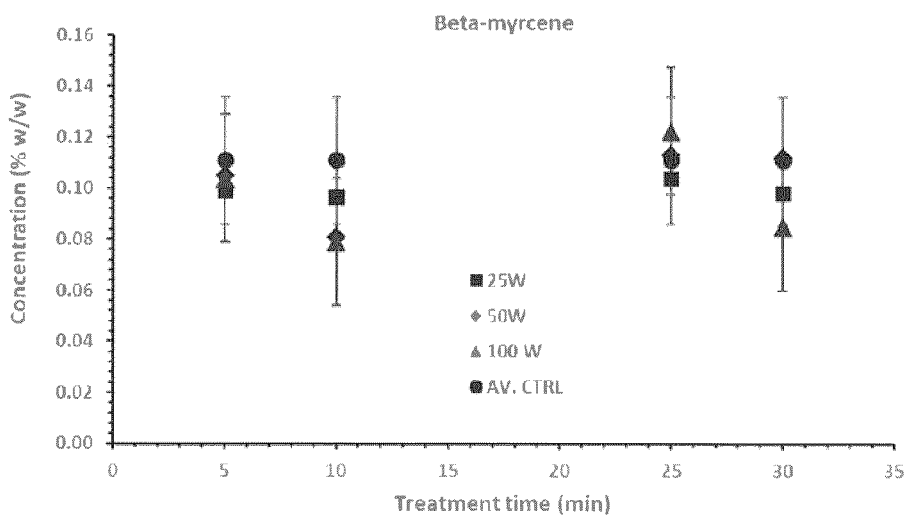
Figure 5C:
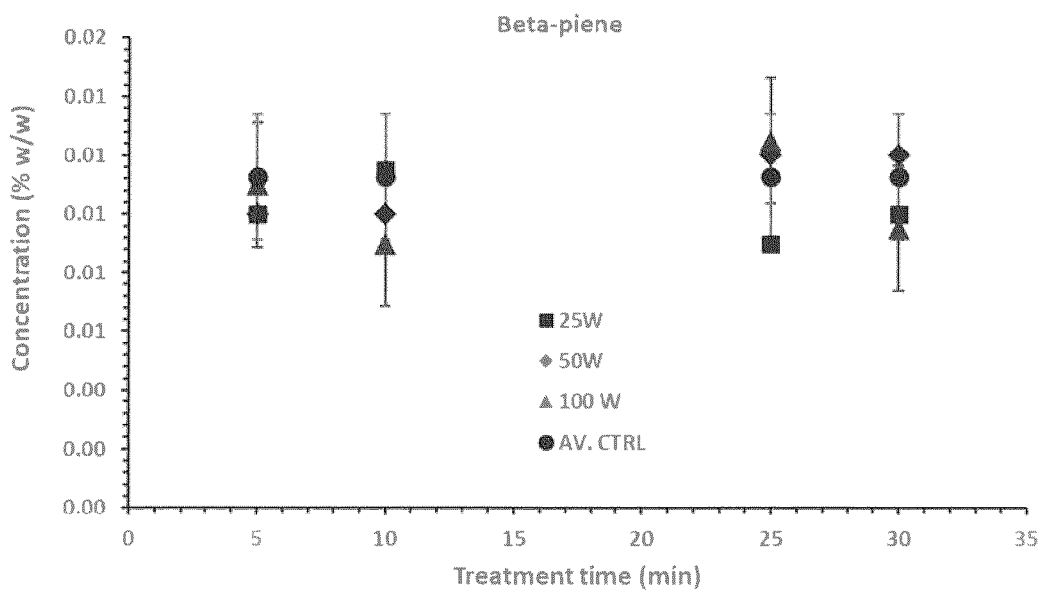
Figure 5D:
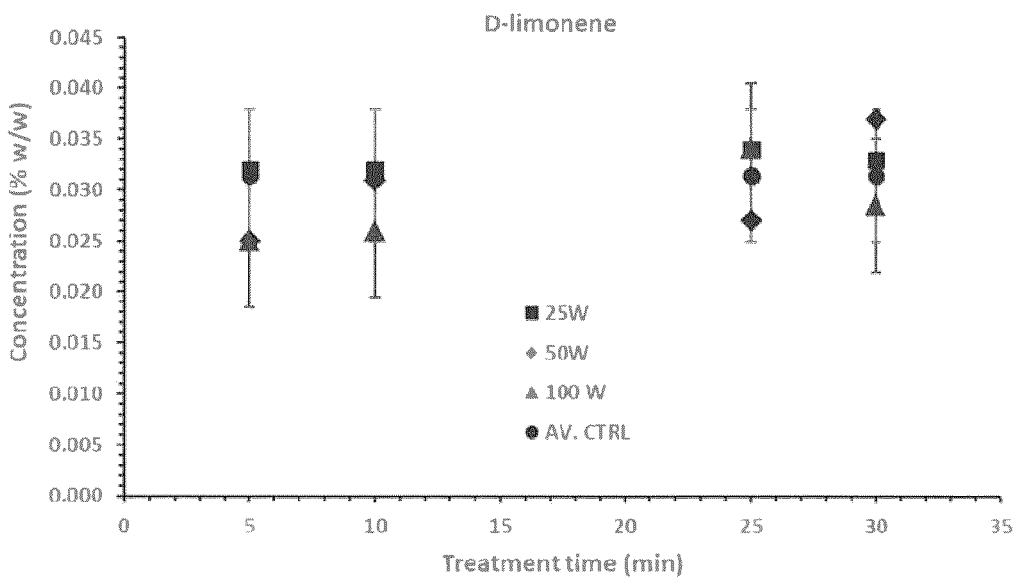
Figure 5E:
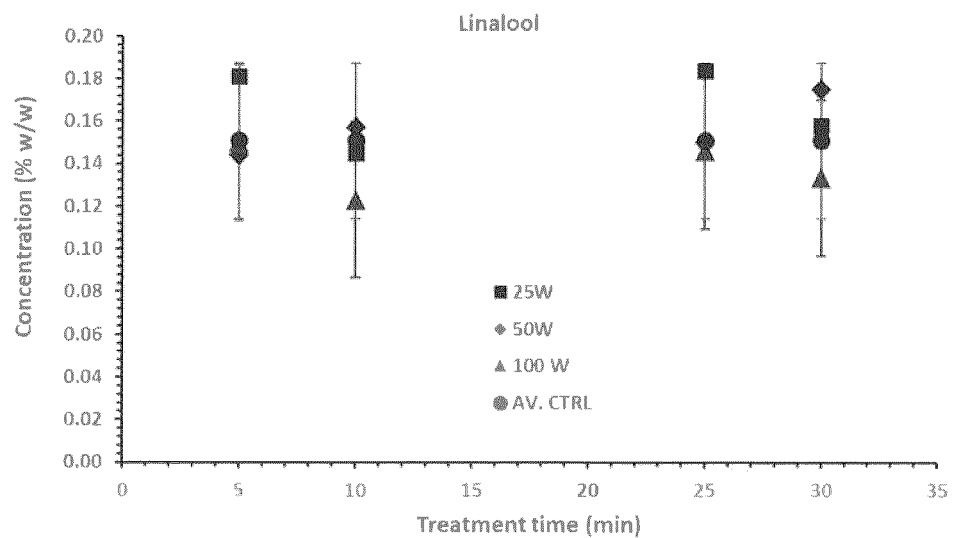
Figure 5F:
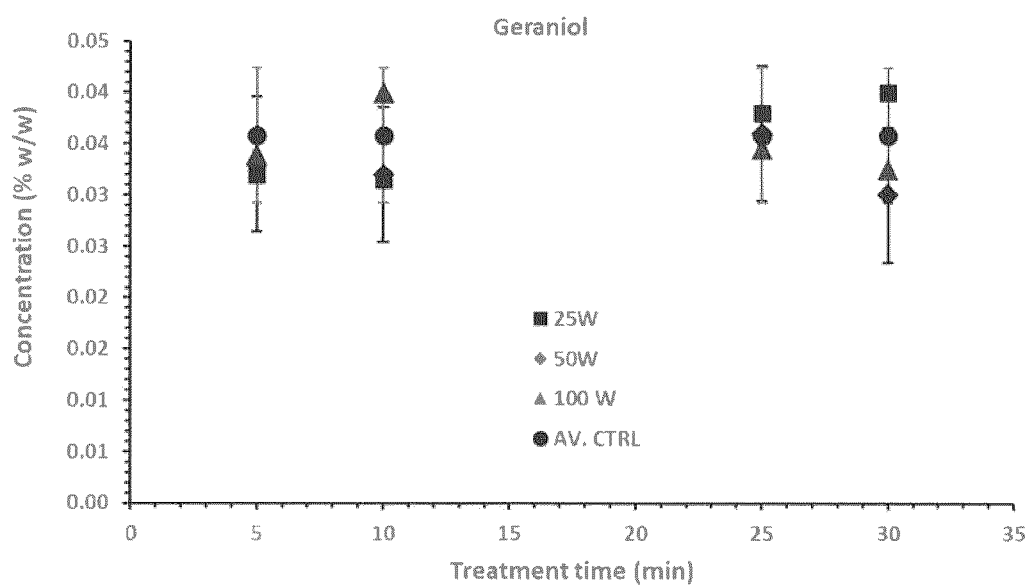
Figure 5G:
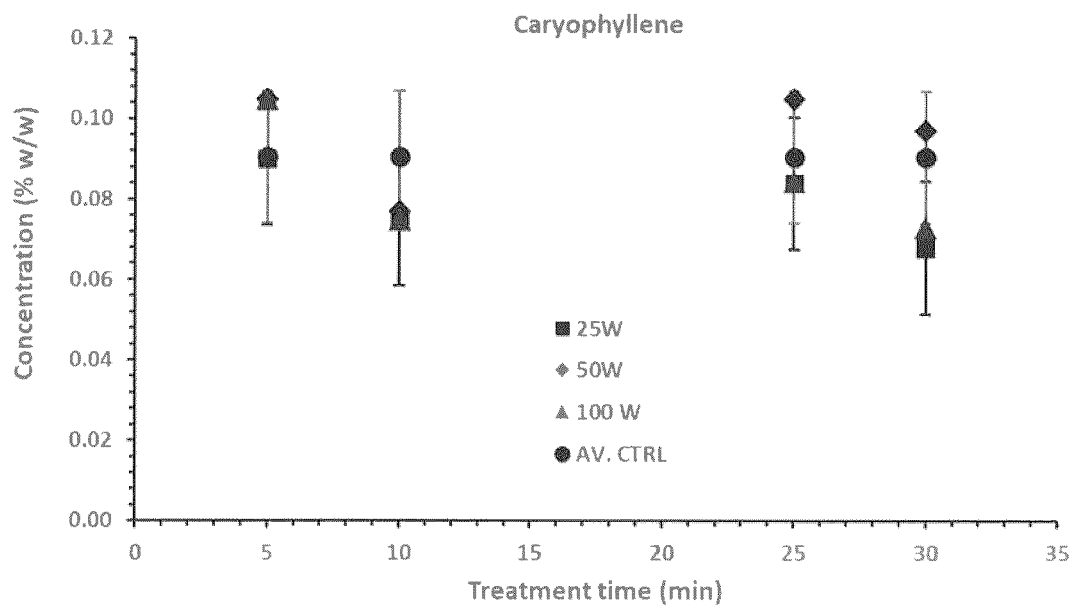
Figure 5H:
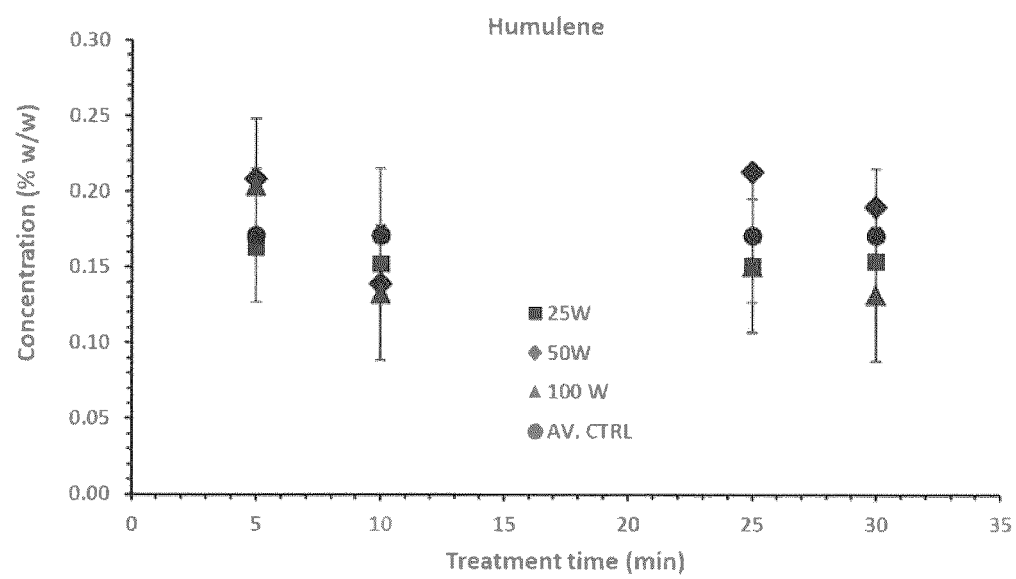

Similar differences in kill rates were also observed for CRM and TB-7 flowers for other plasma conditions. As shown in FIG. 3, surviving populations of yeast and mold are compared after 10 min of $O_2$ plasma treatments at two different levels of input power, 25 and 100 W. For TB-7, 10 min of plasma treatment was required to bring the yeast and mold population to a safe level below 50,000 cfu/g for both power levels. In contrast, 10 min of plasma treatment was not sufficiently effective at both power levels in the case of CRM flowers.

Example 3

Analysis of Effect on Terpenes in Samples Before and After Sterilization

An analysis was conducted to investigate whether cold plasma sterilization has any effect on terpene concentration in hops (*Humulus lupulus*). Dry hop flowers (5 g) were used for the preparation of each sample. Untreated and treated samples were analysed in replicate. Untreated samples were used to determine the baseline concentration of eight terpenes in the hop samples. The eight terpenes were: α-pinene, β-myrcene, β-pinene, D-limonene, linalool, geraniol, caryophyllene, and humulene. Samples were analyzed by gas chromatography-mass spectrometry (GC-MS) to quantify the amount of each of the eight terpenes as a function of plasma treatment conditions such as power and treatment time. Specifically, a Shimadzu GCMS-QP2010SE instrument with EST FLEX Robotic Sampling Platform was used. Each sample was prepared in the following manner: Hops were poured into a clean grinder (e.g., suitable to grid coffee beans) and was pulsed for approximately 10 seconds to obtain hop resin. A clean, dry 20 mL headspace vial was labelled and tarred on a balance. Hops resin (1-3 mg) was transferred to the vial and its mass was recorded. The vial was capped and manually crimped by hand using a Restek 20 mm Manual Crimper. A commercially-available standard solution of 42 different terpenes (available from SPEX CertiPrep) was used for generation of calibration curves. Stock solutions (100 μg/mL) were prepared. A five-point calibration curve was prepared from standards and analyzed to generate calibration curves.

Results of this analysis are presented in FIGS. 4A-4H and 5A-5H. Average values for concentrations of various terpenes as a function of plasma treatment time were determined for A) α-piene; B) myrcene; C)β-pinene; D) limonene; E) linalool; F) geraniol; G) β-caryophyllene; and H) humulene and are graphically presented as percentage of weight. In FIGS. 4A-4H, control (untreated) samples are identified by circles, while treated samples are identified by square symbols for $O_2$ gas pressure of 300 mtorr and plasma power 100 W, and by diamond symbols for $O_2$ gas pressure of 600 mtorr and plasma power 100 W. In FIGS. 5A-5H; control (untreated) samples are shown as circles, treated samples are identified with square symbols for plasma power 25 W, diamond symbols for plasma power 50 W, and triangle symbols for plasma power 100 W. The studies whose results are shown in FIGS. 5A-5H were conducted with a pressure of 300 mtorr and in the presence of the gas $O_2$.

The results depicted in FIGS. 4A-4H and 5A-5H indicate that plasma sterilization had substantially no effect on the concentration of all tested terpenes. These results summarize studies described in Example 3 wherein pressure of $O_2$, power, and sterilization time was varied. Furthermore, all concentrations measured in the treated samples were within one standard deviation from the average values for the control samples. The fact that the plasma treatments are not inducing statistically significant changes in the concentration of terpene molecules demonstrates the effectiveness and utility of this sterilization method.

Equivalents

It will be understood by those skilled in the art that this description is made with reference to certain embodiments and that it is possible to make other embodiments employing the principles of the invention which fall within its spirit and scope.

TABLE 1

Comparison of various terpene molecules in hops and cannabis flowers

| Compound | Terpenes in Hops (wt %) | Terpenes in Cannabis |
|---|---|---|
| myrcene | 16.8-52.4 | 58.72 wt % |
| linalool | 0.2-3.2 | 2.81 wt % |
| β-pinene | 0.2-1.5 | 2.44 wt % |
| α-pinene | 0.2-0.4 | 1.12 wt % |
| α-humulene | 12.6-51.2 | 0.54 wt % |
| β-caryophyllene | 4.1-11.3 | 2.31 wt % |
| limonene | 0.2-1.2 | 17.20 wt % |
| (−)-caryophyllene oxide | 0.6-3.0 | trace |
| geraniol | trace-1.1 | trace to 34 ppm |

SOURCES

Nance, M. R., et al., (2011) *J. Brewing Distilling*, 2, 16-22.
Rossi, S. A., et al., (1996) *J. Nut. Prod.*, 59, 49-51.
Shapira, A., et al., (2019) *Anal. Chem.* 91, 11425-11432.
Eggersdorfer, M. Ulmann's Encyclopedia of Industrial Chemistry, Wiley-VCH Verlag GmbH & Co. KGaA, Weinheim, 2012, 36, 29-35.

I claim:

1. A method for sterilizing plant material, comprising:
disposing plant material on at least one shelf between a pair of electrodes in a spaced relationship in a sub-atmospheric pressure environment that comprises at least one non-toxic, non-polymerizable gas, wherein the sub-atmospheric pressure is in a range of about 0.01 torr to about 10 torr;
applying an electric field to the gas to create a cold plasma cloud, wherein the applying an electric field comprises providing power to the pair of electrodes located inside the sub-atmospheric pressure environment, wherein at least one electrode is a working electrode and at least one electrode is a ground electrode, wherein the cold plasma is formed between the electrodes and wherein the electromagnetic field is applied in continuous mode, and wherein there is no barrier to the cold plasma cloud between the working electrode and the at least one shelf; and
maintaining the plant material in the cold plasma cloud between the electrodes until substantially sterilized plant material is obtained.

2. The method of claim 1, wherein the sub atmospheric pressure is at least 0.01 torr.

3. The method of claim 1, wherein the cold plasma does not deposit residue.

4. The method of claim 1, wherein the plant material comprises leaves and/or flowers.

5. The method of claim 1, wherein the electrodes are located inside the sub-atmospheric pressure environment.

6. The method of claim 1, wherein the electrodes are located close to the sub-atmospheric pressure environment such that the electric field generated by the electrodes creates a cold plasma.

7. The method of claim 1, wherein the plant material is substantially dry.

8. The method of claim 1, wherein the plant material is disposed in one or more layer(s).

9. The method of claim 8, wherein the one or more layer(s) of plant material are disposed on one or more shelves, and wherein each shelf of the one or more shelves has at least two electrodes in a spaced relationship.

10. The method of claim 1, further comprising exposing the substantially sterilized plant material to a sub-atmospheric pressure environment to evacuate plasma and plasma treatment byproducts.

11. The method of claim 1, further comprising controlling temperature of the sub-atmospheric pressure environment.

12. The method of claim 1, wherein the gas is $H_2O$, air, dry air, $H_2$, $O_2$, $N_2$, Ar, He, Ne, Kr, Xe, or a combination thereof.

13. The method of claim 1, wherein gas entering the sub-atmospheric pressure environment has a selected flow rate.

14. The method of claim 1, wherein a range of time of cold plasma treatment is from about 0.5 minutes to about 60 minutes.

15. The method of claim 1, wherein a frequency of the electric field is in a range of about 20 kHz to about 60 kHz.

16. The method of claim 1, wherein the electric field is high frequency, wherein high frequency is 13.56 MHz or 2.45 GHz.

17. The method of claim 1, wherein the maintaining the plant material in the cold plasma cloud comprises maintaining a constant pressure of gas.

18. The method of claim 1, wherein the plant material comprises *cannabis*.

19. The method of claim 1, further comprising tumbling, agitating and/or vibrating the plant material during the plasma treatment.

20. Apparatus for sterilizing plant material, comprising:
a chamber having walls that define a cavity, the chamber having a gas inlet adapted to disperse at least one non-toxic, non-polymerizable gas into the chamber, and a gas outlet;
at least two electrodes in a spaced relationship wherein at least one electrode is a working electrode and at least one electrode is a ground electrode, the at least two electrodes adapted to be electrically connected to an AC power source and generate an AC electric field between them, wherein the electrodes are located inside the chamber;
at least one shelf disposed in the chamber between the at least two electrodes, the at least one shelf adapted to hold a layer of plant material and to allow plasma to pass therethrough;
a pump connected to the gas outlet, the pump adapted to establish a sub-atmospheric pressure of about 0.01 torr to about 10 torr in the presence of gas inflow in the chamber;
wherein the at least two electrodes are adapted to generate a cold plasma cloud in the presence of the at least one non-toxic, non-polymerizable gas, the AC electric field, and the sub-atmospheric pressure;
wherein the cold plasma cloud sterilizes the plant material by killing microorganisms and/or rendering microorganisms inactive, without substantially etching the plant material;
wherein an amount of at least one active constituent in the plant material is substantially unchanged by the sterilizing; and
wherein there is no barrier to the cold plasma cloud between the working electrode and the at least one shelf.

21. The apparatus of claim 20, comprising at least two shelves and at least two pairs of electrodes;
wherein each pair of electrodes comprises two electrodes adapted to be electrically connected to the AC power source and generate an AC electric field between them;
wherein in each shelf of the at least two shelves is disposed between a respective pair of electrodes.

22. The apparatus of claim 21, wherein the shelves are suited to hold plant material in the cold plasma cloud such that the plant material is exposed to the cold plasma on all sides.

23. The apparatus of claim 20, wherein the gas is non-toxic, non-polymerizable, and when the gas is plasma, it leaves behind substantially no residue.

24. The apparatus of claim 23, wherein the gas is $H_2O$, air, dry air, $H_2$, $O_2$, $N_2$, Ar, He, Ne, Kr, Xe, or a combination thereof.

25. The apparatus of claim 20, wherein gas inlet disperses the at least one gas into the chamber at a selected flow rate.

26. The apparatus of claim 20, wherein the AC power source is in a range of about 20 kHz to about 60 kHz.

27. The apparatus of claim 20, wherein the AC power supply is in a radio frequency (RF) of about 13.56 MHZ.

28. The apparatus of claim 20, wherein the AC power supply is in a microwave frequency of about 2.45 GHz.

29. The apparatus of claim 20, wherein the plant material is *cannabis*.

30. The apparatus of claim 20, wherein the plant material comprises leaves and/or flowers.

31. The apparatus of claim 20, wherein one electrode of the at least two electrodes is adapted to allow gas and plasma to pass therethrough.

32. The apparatus of claim 20, wherein the electrodes are located inside the chamber.

33. The apparatus of claim 20, wherein the electrodes are located close to the chamber such that the electric field generated by the electrodes converts the gas to a cold plasma.

34. The apparatus of claim 20, further comprising an agitator that vibrates the shelves.

35. The apparatus of claim 20, further comprising a controller.

* * * * *